(12) United States Patent
Sewiolo et al.

(10) Patent No.: US 10,091,974 B2
(45) Date of Patent: Oct. 9, 2018

(54) METHOD FOR DETERMINING THE SEX OF AN EMBRYO IN AN EGG

(71) Applicant: SIEMENS AKTIENGESELLSCHAFT, München (DE)

(72) Inventors: Benjamin Sewiolo, Obermichelbach OT Rothenberg (DE); Andreas Ziroff, München (DE)

(73) Assignee: Siemens Aktiengesellschaft, München (DE)

( * ) Notice: Subject to any disclaimer, the term of this patent is extended or adjusted under 35 U.S.C. 154(b) by 442 days.

(21) Appl. No.: 14/780,554

(22) PCT Filed: Mar. 17, 2014

(86) PCT No.: PCT/EP2014/055278
§ 371 (c)(1),
(2) Date: Sep. 27, 2015

(87) PCT Pub. No.: WO2014/154513
PCT Pub. Date: Oct. 2, 2014

(65) Prior Publication Data
US 2016/0057977 A1  Mar. 3, 2016

(30) Foreign Application Priority Data

Mar. 27, 2013  (DE) .......... 10 2013 205 426

(51) Int. Cl.
*A01K 45/00* (2006.01)
*A01K 29/00* (2006.01)
(Continued)

(52) U.S. Cl.
CPC .......... *A01K 45/007* (2013.01); *A01K 29/005* (2013.01); *A01K 43/00* (2013.01);
(Continued)

(58) Field of Classification Search
CPC .... A01K 29/005; A01K 43/00; A01K 45/007; A61B 2503/40; A61B 5/055;
(Continued)

(56) References Cited

U.S. PATENT DOCUMENTS 5,508,165 A  4/1996  Halverson et al.
6,029,089 A  2/2000  Hawkins et al.
(Continued)

FOREIGN PATENT DOCUMENTS

CN  1235011 A  11/1999
CN  1165763 C  9/2004
(Continued)

OTHER PUBLICATIONS

Li et al. Steroids, vol. 77, Nov. 29, 2011, pp. 185-192.*
(Continued)

*Primary Examiner* — Maureen Wallenhorst
(74) *Attorney, Agent, or Firm* — Lempia Summerfield Katz LLC

(57) ABSTRACT

The invention relates to a method for determining, the sex of at least one embryo in an egg (12), in which the sex of the embryo is determined by means of at least one detection method which is noninvasive at least with regard to the egg (12), wherein at least one oestradiol value which characterizes the concentration of oestradiol in the egg (12) is determined by means of the noninvasive detection method and the sex is determined as a function of the oestradiol value.

13 Claims, 3 Drawing Sheets

(51) Int. Cl.
*A01K 43/00* (2006.01)
*A61B 5/055* (2006.01)
*A61B 5/145* (2006.01)
*G01N 33/74* (2006.01)
*G01N 33/483* (2006.01)
*G01N 33/68* (2006.01)

(52) U.S. Cl.
CPC .......... *A61B 5/055* (2013.01); *A61B 5/14546* (2013.01); *G01N 33/74* (2013.01); *A61B 2503/40* (2013.01); *G01N 33/483* (2013.01); *G01N 33/689* (2013.01); *Y10T 436/24* (2015.01)

(58) Field of Classification Search
CPC ............. A61B 5/14546; G01N 33/689; G01N 33/483; G01N 33/74; Y10T 436/24; C07J 1/0059; C07J 1/0022
USPC .......... 436/65, 131, 144, 145, 173; 552/625, 552/638
See application file for complete search history.

(56) References Cited

U.S. PATENT DOCUMENTS

| 6,365,339 | B1* | 4/2002 | Daum | .................. G01N 33/743 435/4 |
|---|---|---|---|---|
| 6,506,570 | B1 | 1/2003 | Phelps | |
| 7,041,439 | B2 | 5/2006 | Phelps et al. | |
| 7,950,349 | B1 | 5/2011 | Rollins | |
| 2002/0157613 | A1 | 10/2002 | Phelps et al. | |
| 2003/0096319 | A1 | 5/2003 | Phelps | |

FOREIGN PATENT DOCUMENTS

| CN | 1649487 A | 8/2005 |
|---|---|---|
| CN | 101734984 A | 6/2010 |
| EA | 000734 B1 | 2/2000 |
| EP | 1021717 B1 | 4/2002 |
| FR | 2441378 A1 | 6/1980 |
| WO | WO9814781 A1 | 4/1998 |

OTHER PUBLICATIONS

Chinese Office Action for related Chinese Application No. 201480018815.0 dated Aug. 18, 2016, with English Translation.
German Office Action for related German Application No. 10 2013 205 426.2, dated Jan. 29, 2014, with English Translation.
Jianxin Guo et al: "The Conformations of 17-Estradiol (E2) and 17—Estradiol as Determined by Solution NMR"; Tetrahedron Lett; NIH Public Access; pp. 3465-3469; 2010.
PCT International Search Report and Written Opinion of the International Searching Authority dated Jun. 18, 2014 for corresponding PCT/EP2014/055278, with English Translation.
Russian Decision on grant for related Russian Application No. 2015141006/13(063146) dated Oct. 31, 2016, with English translation.

* cited by examiner

FIG 6

| Position | $\delta_H$ | $\delta_C$ | $^1H$-$^1H$ NOEs |
|---|---|---|---|
| 1 | 7.00 | 126.0 | 2(m); 9(w); 11β(w) |
| 2 | 6.47 | 112.7 | 1(m) |
| 3 | - | 154.8 | |
| 4 | 6.39 | 114.9 | 6α(m); 6β(w) |
| 5 | - | 137.1 | |
| 6α | 2.65 | 29.1 | 4(m); 7α(w) |
| 6β | 2.68 | | 4(w); 7β(w); 8(w) |
| 7α | 1.19 | 26.9 | 6α(w); 7β(s); 9(m) |
| 7β | 1.74 | | 6β(w); 7α(s); 8(m) |
| 8 | 1.24 | 38.7 | 7β(m); 18(m) |
| 9 | 2.03 | 43.5 | 7α(m); 11α(w); 14(w) |
| 10 | - | 130.4 | |
| 11α | 2.19 | 26.0 | 9(w); 11β(s); 12α(w) |
| 11β | 1.27 | | 11α(s); 18(m) |
| 12α | 1.13 | 36.5 | 11α(w); 12β(s); 14(w); 17(w) |
| 12β | 1.80 | | 12α(s); 18(w) |
| 13 | - | 42.8 | |
| 14 | 1.07 | 49.5 | 9(w); 12α(w); 15α(m) |
| 15α | 1.55 | 22.7 | 14(m); 15β(s); 16α(w); 16β(w) |
| 15β | 1.21 | | 15α(s); 16α(w); 18(m) |
| 16α | 1.85 | 29.8 | 15α(w); 15β(w); 16β(s); 17(m) |
| 16β | 1.34 | | 15α(w); 16α(s); 17(w); 18(w) |
| 17 | 3.48 | 80.0 | 12α(w); 16α(m); 16β(w) |
| 18 | 0.63 | 11.2 | 8(m); 11β(m); 12β(w); 15β(m); 16β(w) |

METHOD FOR DETERMINING THE SEX OF AN EMBRYO IN AN EGG

The invention relates to a method for determining the sex of an embryo in an egg, in particular a chicken egg, as per the preamble of patent claim 1.

In chicken farming, male chicks are economically undesired since they, or the cockerels, do not lay eggs, and barely gain weight. This is why male chicks, once they have hatched, are usually sorted and culled. In addition to the cost for ensuring that animal protection aspects are met, additional costs arise since all eggs, be it eggs with male embryos or eggs with female embryos, must be incubated. Sexing in the egg might prevent this.

Research already knows very complex methods of sexing the embryo within the egg, in particular within the chicken egg, by methods which are invasive in respect of the egg. Here, for example, a hole of a size of a few millimeters is made in the eggshell by means of a laser. The blastodisk of the egg is located without touching with the aid of OCT (optical coherence tomography). Finally, sexing is carried out with the aid of infrared spectroscopy.

WO 98/14781 A1 discloses a method for sexing at least one embryo in an egg, where sexing is performed by means of at least one determination method which is noninvasive at least in respect of the egg. By means of the determination method, an estrogen content in the egg is determined, and the embryo is sexed on the basis of the estrogen content which has been determined. The estrogen may be estradiol.

From U.S. Pat. No. 6,029,089 it can be seen that a method for sexing at least one embryo in an egg, in particular in a chicken egg, is known. In this method, sexing is performed by means of at least one determination method which is noninvasive in respect of the egg. The noninvasive determination method which is carried out is, for example, a magnetic resonance tomography method. The reproduction organs of the embryo are examined by means of the noninvasive determination method. Finally, the embryo is sexed on the basis of this examination.

This method, too, is complex and therefore costly; moreover, the egg must be incubated for a long time so as to examine thereafter the reproduction organs of the at least partially developed embryo.

It is therefore an object of the present invention to further develop a method, of the kind cited at the outset, for sexing within an egg, in particular within a chicken egg, in such a way that particularly early sexing is made possible in a particularly simple and therefore time- and cost-saving method.

This object is achieved by a method with the features of patent claim 1. Advantageous embodiments with expedient and nontrivial developments of the invention are specified in the remaining claims.

In such a method for sexing of at least one embryo in an egg, in particular in a bird's egg and in particular in a chicken egg, the embryo is sexed by means of at least one determination method which is noninvasive at least in respect of the egg.

For particularly simple, time- and cost-saving sexing and particularly early sexing in respect of the egg's age it is provided that at least one estradiol value which characterizes the estradiol concentration in the egg is determined by means of the noninvasive determination method. The sex is determined as a function of the estradiol value determined.

In accordance with the invention, the chemical shift of hydrogen atoms and/or of carbon atoms in the egg is determined by means of the noninvasive determination method, in particular by means of the imaging method and in particular by means of magnetic resonance spectroscopy, the estradiol value being determined as a function of the shift which has been determined. This allows especially precise conclusions to be drawn regarding the estradiol value and, ultimately, regarding the expected sex of the embryo which may or may not develop in the future.

Sexing the embryo by means of the method according to the invention means that the embryo need not, or not yet, be present in the egg. In other words, the embryo need not, or not yet, be fully formed. If the embryo is not, or not yet, or not fully, formed, sexing the embryo is understood as meaning that the embryo which may or may not develop in the future is sexed. This is because the method according to the invention makes it possible to determine the sex without the embryo already having developed. In other words, the method can be carried out in a state, or at an age, of the egg in which the embryo has not developed at all, has only developed in part or has already developed fully. Preferably, the method is carried out when the embryo has not yet or only partly developed. This means that the sex of the embryo which may or may not develop in the future is determined, and/or that the sex which the embryo might have if it were to develop is determined.

Estradiol is a female sex hormone which is present in the egg and whose concentration in the egg is determined by means of the noninvasive determination method. Determining the concentration of the female sex hormone estradiol allows the early and, with a very high likelihood, correct determination of the sex of the embryo which may or may not develop in particular only at a later point in time, i.e. in the future. As a consequence, the effort of the measures described at the outset can be avoided or at least kept to a minimum since the corresponding measures can be taken before the developing animal, in particular the bird and in particular the chick, hatches from the egg.

Moreover, it is not provided and not necessary within the scope of the method according to the invention to open the eggshell and to remove components or substances from the egg. The time and costs required for sexing can therefore be kept particularly low.

In a particularly advantageous embodiment of the invention, the noninvasive determination method which is carried out is an imaging method, in particular a magnetic resonance spectroscopy method. This allows the concentration of estradiol in the egg to be determined particularly quickly and precisely so that the sex, or the expected sex, can with a very high probability be determined correctly.

It has shown to be expedient to determine the chemical shift in the unit parts per million (ppm). To determine the chemical shift of hydrogen atoms within the egg, one will, for example, carry out a $^1$H spectroscopy. To determine the chemical shift of carbon atoms in the egg, one will, for example, carry out a $^{13}$C spectroscopy. This allows the estradiol value to be determined particularly accurately so that, in turn, the sex can, with a very high probability, be determined correctly.

In a particularly advantageous embodiment of the invention, at least one testosterone value which characterizes the testosterone concentration in the egg is carried out by means of the noninvasive determination method. Furthermore, a ratio of the estradiol value to the determined testosterone value is determined, the sex being determined as a function of the comparison. In other words, the female sex hormone estradiol is compared with the male sex hormone testosterone in the egg. Then, it is possible with a very high probability to correctly determine, with reference to this comparison, the sex before the embryo and in particular the chick have developed partly or fully.

For obtaining especially meaningful results, it has shown to be especially advantageous to determine the estradiol value and, if appropriate, the testosterone value before the thirtieth day of incubation of the egg.

The method also makes possible especially good results when the estradiol value and, if appropriate, the testosterone value are determined before the twentyfifth, in particular approximately on the seventeenth, day of incubation. By doing so, the measures which, as the case may be, may be carried out as a function of the sex determined and in respect of the egg may be carried out particularly early so that the costs can be kept low and a very good animal protection aspect can be achieved.

It has shown to be particularly expedient to determine the estradiol value and the testosterone value on the same day of incubation of the egg. This allows a particularly good comparison of the estradiol value and the testosterone value with each other.

In contrast to traditional methods for sexing within the egg, in particular within the chicken egg, the method may already be carried out after a very short, in terms of time, incubation of the egg, i.e. after a very low number of incubation days. At the same time, a very precise sexing can be achieved in a noninvasive fashion.

Other advantages, features and details of the invention can be seen from the subsequent description of a preferred embodiment and by reference of the drawing. The features and combinations of features mentioned hereinabove in the description, and the features and combinations of features mentioned hereinbelow in the description of the figures and/or in the figures alone may be used not only in the combination specified in each case, but also in other combinations or alone, without departing from the scope of the invention.

In the drawing,

FIG. 1 shows a schematic and partial section of a side view of a device as per a first embodiment for carrying out a method for sexing at least one embryo in a chicken egg, in which at least one estradiol value which characterizes the estradiol concentration in the chicken egg is determined by means of a noninvasive determination method in the form of magnetic resonance spectroscopy, where the sex of the embryo which may or may not develop in the future is determined as a function of the estradiol value which has been determined;

FIG. 6 shows a table with the chemical shift of estradiol.

Figure 1:
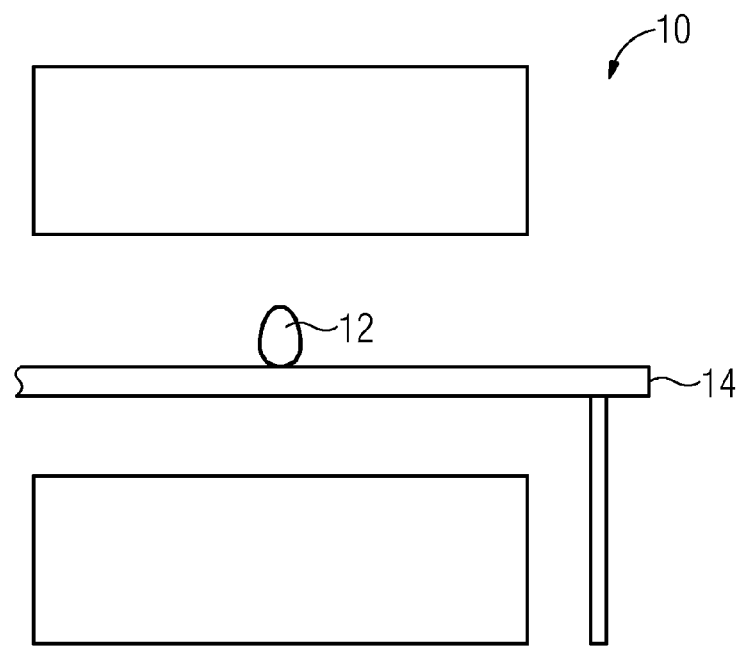

FIG. 1 shows a nuclear spin tomograph 10 as per a first embodiment, by means of which a determination method in the form of a magnetic resonance spectroscopy is carried out for sexing an embryo in an egg 12. To this end, the egg 12 is arranged on an examination table 14 inside the nuclear spin tomograph 10. The determination method, or the magnetic resonance spectroscopy, is noninvasive in relation to the egg 12. This means that in order to perform the sexing the shell of the egg 12 is not opened and no components or substances are removed from the egg 12. FIG. 1 only shows the one egg 12. Of course, it is also possible to arrange in the nuclear spin tomograph 10 a plurality of eggs at the same time and to examine them for the respective sex.

Determining the sex, or sexing, the embryo in the egg 12 is understood as meaning that the sex of the embryo which may or may not develop in the future is determined in the egg 12. In other words, the embryo in the egg 12 need not be developed or fully developed in order to be sexed. This means that the sex being determined is the sex which the embryo would have if it were to develop.

This is because the method makes it possible to determine the sex of the embryo which may or may not develop in the future, in other words the embryo which might develop, at a very early age of the egg 12, i.e. especially early. For example, the sex is determined approximately on the seventeenth incubation day of the egg 12. This is possible since—as is yet to be explained in what follows—it is not the embryo itself, which is not yet even present in the egg 12, which is examined by means of magnetic resonance spectroscopy. What is determined by means of the noninvasive determination method in the form of the magnetic resonance spectroscopy is at least one estradiol value which characterizes the concentration of estradiol, in particular 17β-estradiol, in the egg 12, the sex being determined as a function of the estradiol value which has been determined.

Figure 2:
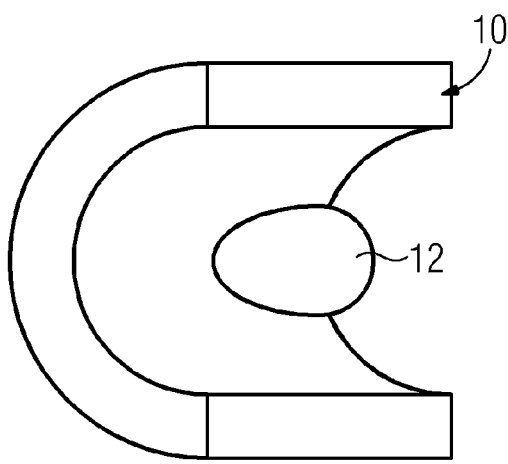
FIG. 2 shows a schematic, perspective section of a side view of the device as per a second embodiment.
Figure 3:
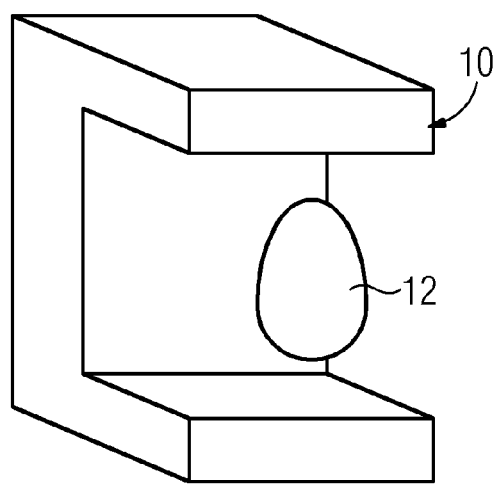
FIG. 3 shows a schematic, perspective section of a side view of the device as per a third embodiment.
Figure 4:
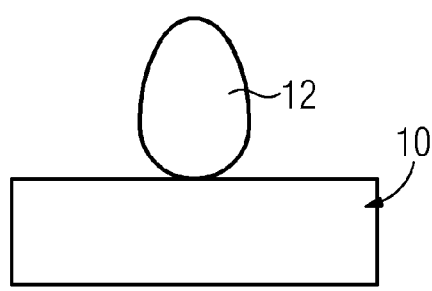
FIG. 4 shows a schematic side view of the device as per a fourth embodiment.

As can be seen from FIGS. 2, 3 and 4, it is possible to employ various embodiments of the nuclear spin tomograph 10 for sexing. Here, the egg 12 is arranged in each case in what is known as the viewing area of the respective nuclear spin tomograph 10 so as to carry out the determination method. In other words, the egg 12 is arranged in a respective scanning range of the respective nuclear spin tomograph 10 so as to scan the egg 12 by means of the nuclear spin tomograph 10 and to be able to determine the estradiol value.

Figure 5:
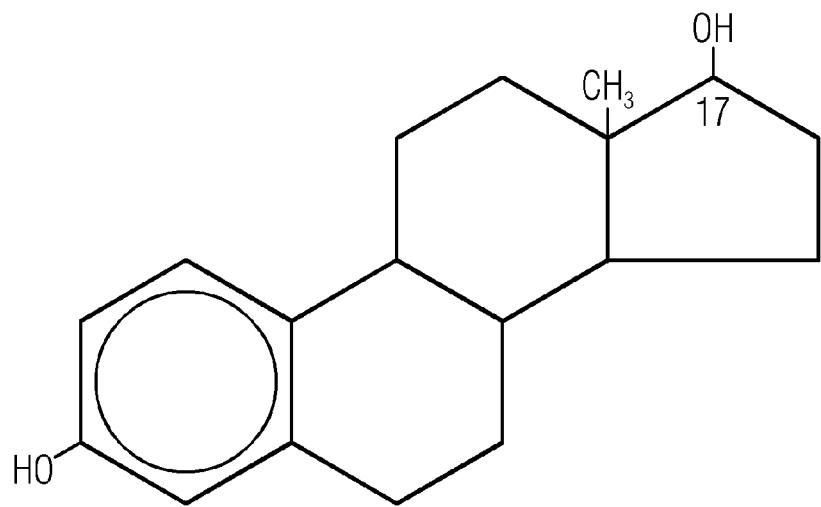
FIG. 5 shows the structural formula of estradiol.

FIG. 5 shows the structural formula of 17β-estradiol. The chemical shift of hydrogen and/or carbon atoms in the egg 12 is determined by means of magnetic resonance spectroscopy in the unit parts per million (ppm). For example, a $^1$H or $^{13}$C spectroscopy is carried out to this end.

FIG. 6 shows a table of the chemical shift of 17β-estradiol, $\delta_H$ referring to the chemical shift of the H atoms of 17β-estradiol and $\delta_C$ the chemical shift of the C atoms of 17β-estradiol. NOEs refers to the nuclear Overhauser effects, where s refers to strong nuclear Overhauser effect intensities, n medium nuclear Overhauser effect intensities and w weak nuclear Overhauser effect intensities. In addition, the nuclear Overhauser effect intensities were converted into upper limiting distance conditions of 2.7, 3.5 and 5.0 Angstrom in the molecular dynamics calculation.

Magnetic resonance spectroscopy can furthermore be used for determining, in a noninvasive manner relative to the egg 12, a testosterone value which characterizes the concentration of testosterone in the egg 12. Finally, a ratio of the estradiol value to the testosterone value is formed, and the sex is determined as a function of this ratio. This makes it possible to correctly determine or predict, with an especially high probability, the sex at a very early point in time, i.e. after only a very low number of incubation days of the egg 12. The determination of the female sex hormone estradiol, or 17β-estradiol, respectively, and of the male sex hormone testosterone make it possible here to arrive at especially meaningful results, so that a correct statement can be made with a very high probability on whether a male or a female chick will or would develop in the egg 12.

Since the method can be carried out before the chick develops and before it hatches, it is also possible to take especially early suitable measures as a function of the sex which has been determined or found out so as to ensure the development of the embryo or of the chick, or to prevent the development or the further development.

We claim:

1. A method for determining a sex of at least one embryo in an egg, the method comprising:
    determining the sex of the embryo by at least one determination method that is noninvasive at least in relation to the egg, wherein, by the at least one noninvasive determination method, at least one estradiol value that characterizes a concentration of estradiol in the egg is determined, the sex being determined as a function of the estradiol value; and
    determining a shift of hydrogen atoms, carbon atoms, or hydrogen atoms and carbon atoms in the egg by the at least one noninvasive determination method, and determining the at least one estradiol value as a function of the determined shift.

2. The method of claim 1, wherein an imaging method is carried out as the at least one noninvasive determination method.

3. The method of claim 2, wherein the imaging method comprises magnetic resonance spectroscopy.

4. The method of claim 2, further comprising determining at least one testosterone value that characterizes a concentration of testosterone in the egg by the at least one noninvasive determination method and a ratio of the at least one estradiol value to the at least one testosterone value, the sex being determined as a function of the ratio.

5. The method of claim 2, wherein the at least one estradiol value is determined before a thirtieth incubation day of the egg.

6. The method of claim 1, further comprising determining at least one testosterone value that characterizes a concentration of testosterone in the egg by the at least one noninvasive determination method and determining a ratio of the at least one estradiol value to the at least one testosterone value, the sex being determined as a function of the ratio.

7. The method of claim 6, wherein the at least one estradiol value and the at least one testosterone value are determined on a same incubation day of the egg.

8. The method of claim 6, wherein the at least one estradiol value is determined before a thirtieth incubation day of the egg.

9. The method of claim 1, wherein the at least one estradiol value is determined before a thirtieth incubation day of the egg.

10. The method of claim 9, wherein the at least one estradiol value is determined before a twenty-fifth incubation day.

11. The method of claim 10, wherein the at least one estradiol value is determined on a seventeenth incubation day.

12. The method of claim 10, wherein the at least one estradiol value and at least one testosterone value are determined on a same incubation day of the egg.

13. The method of claim 9, wherein the at least one estradiol value and at least one testosterone value are determined on a same incubation day of the egg.

* * * * *